US011436758B2

(12) United States Patent
Ko et al.

(10) Patent No.: US 11,436,758 B2
(45) Date of Patent: Sep. 6, 2022

(54) METHOD AND SYSTEM FOR MEASURING BIOCHEMICAL INFORMATION USING COLOR SPACE CONVERSION

(71) Applicant: Fitpet Co., Ltd., Seoul (KR)

(72) Inventors: Jung Uk Ko, Seoul (KR); Yeon Chul Rim, Seoul (KR); Kyung Hwa Chae, Seoul (KR)

(73) Assignee: Fitpet Co., Ltd., Seoul (KR)

( * ) Notice: Subject to any disclaimer, the term of this patent is extended or adjusted under 35 U.S.C. 154(b) by 285 days.

(21) Appl. No.: 16/838,271

(22) Filed: Apr. 2, 2020

(65) Prior Publication Data

US 2021/0158572 A1 May 27, 2021

(30) Foreign Application Priority Data

Nov. 22, 2019 (KR) .................. 10-2019-0151476

(51) Int. Cl.
| | |
|---|---|
| *G06T 7/90* | (2017.01) |
| *G01J 3/46* | (2006.01) |
| *G01J 3/52* | (2006.01) |
| *G01N 21/78* | (2006.01) |
| *G01N 33/493* | (2006.01) |
| *G06T 7/00* | (2017.01) |

(52) U.S. Cl.
CPC ............... *G06T 7/90* (2017.01); *G01J 3/462* (2013.01); *G01J 3/463* (2013.01); *G01J 3/52* (2013.01); *G01N 21/78* (2013.01); *G01N 33/493* (2013.01); *G06T 7/0014* (2013.01); G06T 2207/10024 (2013.01)

(58) Field of Classification Search
CPC .............. G06T 7/90; G06T 7/0014; G06T 2207/10024; G06T 7/11; G06T 5/20; G06T 5/40; G01J 3/462; G01J 3/463; G01J 3/52; G01N 21/78; G01N 33/493; G01N 21/293; G01N 2021/7759; G01N 21/8483
See application file for complete search history.

(56) References Cited

U.S. PATENT DOCUMENTS

| 8,023,736 B2 * | 9/2011 | Tsukada .................... H04N 9/73 382/173 |
| 10,304,188 B1 * | 5/2019 | Kumar .................... G06V 20/69 |
| 11,044,450 B2 * | 6/2021 | Afifi .......................... G06T 5/40 |
| 2016/0080548 A1 * | 3/2016 | Erickson ........... H04M 1/72409 382/128 |

(Continued)

FOREIGN PATENT DOCUMENTS

| KR | 10-1720203 B1 | 3/2017 |
| WO | WO 2015/038717 A1 | 3/2015 |

*Primary Examiner* — Aaron W Carter
(74) *Attorney, Agent, or Firm* — The PL Law Group, PLLC

(57) ABSTRACT

A method according to an embodiment of the present invention includes acquiring an image of a urine test kit equipped with a biochemical sample rod including a plurality of pad cells including a plurality of sub-pad cells, extracting at least one potential RGB value from the image by means of a potential color extractor, and converting and analyzing the at least one potential RGB value using a plurality of color spaces included in a color space conversion engine and a color space analysis engine by means of an analyzing unit. The plurality of color spaces are randomly generated, and a color space having a smallest distance value from the potential RGB value is determined as an optimal color space.

11 Claims, 12 Drawing Sheets

(56) References Cited

U.S. PATENT DOCUMENTS

| | | | |
|---|---|---|---|
| 2017/0053400 A1* | 2/2017 | Shen | G01N 33/493 |
| 2017/0237961 A1* | 8/2017 | Barron | G06T 5/001 |
| | | | 348/223.1 |
| 2019/0346429 A1* | 11/2019 | Harris | B01L 3/5023 |
| 2020/0126226 A1* | 4/2020 | Adiri | G06T 7/0012 |
| 2020/0126261 A1* | 4/2020 | Fu | G06V 10/56 |
| 2020/0209214 A1* | 7/2020 | Zohar | G16H 70/00 |
| 2020/0242809 A1* | 7/2020 | Limburg | G01J 3/46 |
| 2020/0249220 A1* | 8/2020 | Kim | A61B 10/00 |
| 2020/0376491 A1* | 12/2020 | Deng | G06V 10/56 |
| 2021/0133974 A1* | 5/2021 | Makino | A61B 1/000094 |
| 2021/0158572 A1* | 5/2021 | Ko | G01N 33/493 |
| 2021/0208081 A1* | 7/2021 | Tayfun | G01N 33/573 |
| 2021/0237053 A1* | 8/2021 | Wennberg | G06T 7/13 |

* cited by examiner

METHOD AND SYSTEM FOR MEASURING BIOCHEMICAL INFORMATION USING COLOR SPACE CONVERSION

CROSS-REFERENCE TO RELATED APPLICATION AND CLAIM OF PRIORITY

This application claims priority to and the benefit of Korean Patent Application No. 10-2019-0151476, filed on Nov. 22, 2019, the disclosure of which is incorporated herein by reference in its entirety.

BACKGROUND

1. Technical Field

Embodiments of the present invention relate to a method for measuring biochemical information using color space conversion, and more particularly, to a method for measuring biochemical information to produce a more reliable result with color space conversion and enhance market competitiveness when state information of a biochemical sample is detected using an image sensor.

2. Background Art

Recently, a single-person household lifestyle is increasingly becoming popular, and the number of single-person households is growing day by day. As the number of single-person households increases, demands for pets is also increasing rapidly and thus the related market is also growing rapidly. Further, as the demands for pets increase, interests in health care of pets are also increasing day by day.

Regarding the health care of pets, regular screenings are necessary, but the regular screenings for pets were problematic for a variety of reasons, such as time-related problems that require a visit to a veterinarian, and cost-related issues, which are high screening costs. Thus, self-diagnosis techniques at home with kits were developed but were somewhat cumbersome for general users because most self-diagnosis with kits were based on pet's blood.

In order to solve the above-described disadvantages, a pet diagnosis kit having pads for absorbing pet urine and feces to analyze disease information regarding a pet was developed. However, the conventional pet diagnosis kit was inconvenient to attach to a pet because the user of the kit should fasten the pad of the pet diagnosis kit with a fastening band before using the pet diagnosis kit. Also, if pet's urine and feces are not absorbed enough or unevenly absorbed to the pad of the pet diagnosis kit, it was difficult for the pet diagnosis kit to obtain accurate results, which can reduce the accuracy of diagnosis.

Meanwhile, the background of the invention has been written in order to facilitate an understanding of the present invention. It should not be construed that the matters described in the background of the invention are acknowledged to exist as the prior art.

SUMMARY

An embodiment of the present invention is directed to providing a method of detecting biochemical information using color space conversion, the method being capable of detecting an accurate color on the basis of color space conversion in a urine test reference color sheet and test pad in which a distorted color appears unless it is an ideal environment when an image sensor is used for imaging.

An embodiment of the present invention is also directed to providing a biochemical information detecting method capable of deriving an accurate result even when only some pad cells are discolored by dividing the area of a test pad and performing convolution on a color of the divided area, and extracting representative R, G, and B values that have no distortion even without the entire color data of a desired area.

An embodiment of the present invention is also directed to providing a method of detecting biochemical information using color space conversion, the method being capable of providing a certain result value regardless of ambient environments by applying a color constancy algorithm.

An embodiment of the present invention is also directed to providing a method of measuring biochemical information using color space conversion, the method being capable of effectively improving market competitiveness by performing a reliable real-time test using minimal resources.

The present invention are not limited to the above-described objects, and other objectives that are not described herein will be apparently understood by those skilled in the art from the following description.

According to an aspect of the present invention, there is a method of measuring biochemical information using color space conversion, the method including acquiring an image of a urine test kit equipped with a biochemical sample rod including a pad cell, the urine test kit including a plurality of colorimetric table cells; extracting a potential color of a first color space of the plurality of colorimetric table cells and the pad cell from the image; extracting the potential color as a color of a color space other than the first color space; selecting a colorimetric table cell having a color closest to any one of a plurality of pad cells of the other color space from among a plurality of colorimetric table cells on the basis of the color of the other color space; and diagnosing urine by determining a result index on the basis of a colorimetric table cell index having a color closest in the color space other than the first color space.

Also, the method may further include extracting the potential color of the first color space as colors of the second to $\ell^{th}$ color spaces in the case of an integer $\ell$ of three or more; finding $t^{th}$ color distances between a colorimetric table cell having a color closest in the $t^{th}$ color spaces (here, $2 \le t \le \ell$) and colors obtained by converting the color of the pad cell into the colors of the $t^{th}$ color spaces and selecting a color space having the smallest color distance among the $t^{th}$ color distances; and determining a colorimetric table cell index having a color closest in the selected color space as the result index when the urine is diagnosed by determining the result index on the basis of the colorimetric table cell index having the color closest in the other color space.

Also, the method may further include extracting the potential color of the first color space as a color of a randomly selected one of the second to $\ell^{th}$ color spaces in the case of a randomly selected number $\ell$ ($\ell$ is an integer of three or more); finding $t^{th}$ color distances between a colorimetric table cell having a color closest in the $t^{th}$ color spaces (here, $2 \le t \le \ell$) and colors obtained by converting the color of the pad cell into the colors of the $t^{th}$ color spaces and selecting a color space having the smallest color distance among the $t^{th}$ color distances; determining a colorimetric table cell index having a color closest in the selected color space as the result index when the urine is diagnosed by determining the result index on the basis of the colorimetric table cell index having the color closest in the other cell space; and deriving a final index by repeating the selecting of the color space and the determining of the result index a predetermined number N of times after re-determining any number $\ell$ and re-extracting a color of a colorimetric table cell and a pad cell extracted from the selected color space as the color of the randomly selected one of the second to $\ell^{th}$ color spaces.

Also, the method may further include diagnosing the urine according to a final index that is most frequently derived by repeating the extracting of the potential color of the first color space as the color of the randomly selected one of the second to $l^{th}$ color spaces, the selecting of the color space, the determining of the result index, and the deriving of the final index.

Also, the extracting of the potential color of the first color space may include generating a color matrix from the color of the first color space extracted from a plurality of color extraction points included in the pad cell, and extracting a potential color of each of the plurality of pad cells on the basis of a convolution value of the color matrix and a convolution filter.

Also, the extracting of the potential color may include calculating a plurality of feature values through convolution of the color matrix and the convolution filter and extracting a value having the highest density from a histogram generated by the plurality of feature values as the potential color.

Also, the method may further include performing white balancing such that the image having an inconstant color distribution has a constant color value.

Also, the performing of white balancing may include correcting a color variation of the image such that the image has certain color development regardless of external factors using a color constancy algorithm.

Also, the performing of white-balancing may further include converting an image having an inconstant color value into a histogram; re-converting the histogram to be divided into predetermined displacement values; extracting rank values from the re-converted histogram; and implementing an image having a constant color value on the basis of the predetermined displacement values and the rank values, and the image having the constant color value may be implemented using the following equation:

$$\frac{(Output_{max} - Output_{min}) \times (Input - Histogram_{min})}{Histogram_{max} - Histogram_{min}} + Output_{min}$$

where $Output_{max}$ indicates an extracted maximal displacement value, $Output_{min}$ indicates an extracted minimal displacement value, Input indicates an input value, $Histogram_{min}$ indicates a minimal histogram rank, and $Histogram_{max}$ indicates a maximal histogram rank.

Also, the first color space and the other color space may include at least one of RGB, HSV, $c_1c_2c_3$, $\ell_1\ell_2\ell_3$, $m_1m_2m_3$, and Lab.

Also, the method may further include combining the color matrix and a colorimetric table matrix generated using the potential color of the colorimetric table cell.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
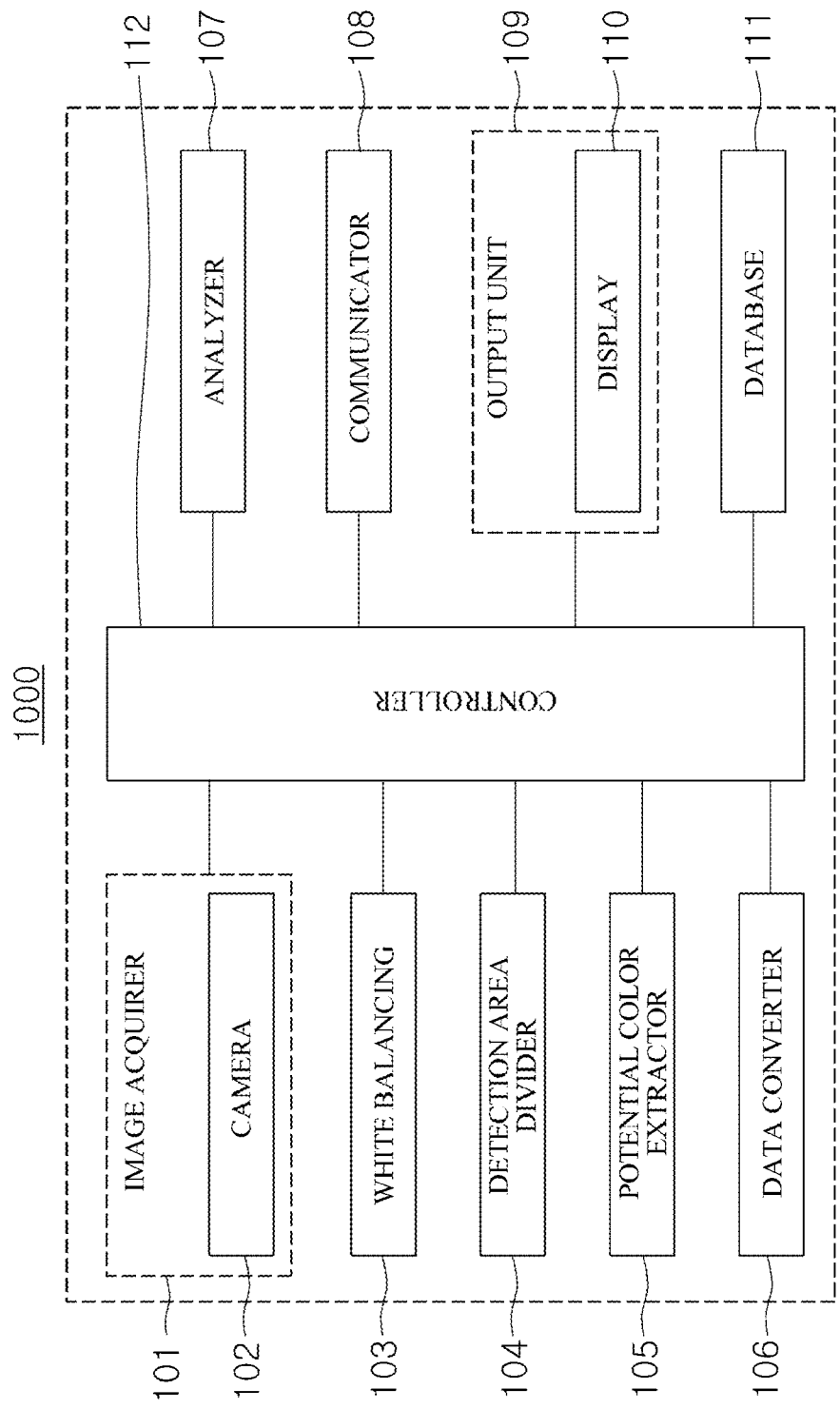
FIG. 1 is a block diagram of a biochemical information detection system according to an embodiment of the present invention.

Advantages and features of the present invention and methods to achieve them will become apparent from the description of embodiments herein below with reference to the accompanying drawings. However, the present invention is not limited to embodiments disclosed herein and may be implemented in various forms. The embodiments are provided for making the disclosure of the prevention invention thorough and for fully conveying the scope of the present invention to those skilled in the art. It is to be noted that the scope of the present invention is defined by the claims.

The figures, dimensions, ratios, angles, numbers, and the like disclosed in the drawings for describing the embodiments of the present invention are merely illustrative and are not limited to matters shown in the present invention. Further, in describing the present invention, detailed descriptions on well-known technologies will be omitted when it is determined that they may unnecessarily obscure the gist of the present invention. Terms such as "including" and "having" used herein are intended to allow other elements to be added unless the terms are used with the term "only." Any references to the singular may include the plural unless expressly stated otherwise.

Components are interpreted to include an ordinary error range even if not expressly stated.

The features of various embodiments of the present invention may be partially or entirely bonded to or combined with each other and may be interlocked and operated in technically various ways as can be fully understood by a person having ordinary skill in the art, and the embodiments may be carried out independently of or in association with each other.

A biochemical information detection system 1000 of the present invention and elements thereof will be described below with reference to FIGS. 1 and 2.

FIG. 1 is a block diagram of a biochemical information detection system according to an embodiment of the present invention. FIG. 2 is an exemplary diagram showing a urine test kit having a biochemical sample rod according to an embodiment of the present invention.

The biochemical information detection system 1000 is a system capable of detecting accurate biochemical information based on images collected from a user terminal 100 in order to measure various biochemical information related to pets from their urine. In the present invention, biochemical information refers to various information regarding compositions, suspected diseases or pets' body (weight, height) which are derived by examining the pets' urine with biochemical sample bar 220 of the present invention. For example, the compositions may include glucose, bilirubin, ketone, specific gravity, blood, protein, nitrite, urobilinogen, etc., and may include other compositions that with the information of the compositions in the pet's urine, pets can be diagnosed to have suspected diseases. Further, the biochemical information may be classified by time period, type of pet, and the like and may be described in the form of a table, an image, a graph, and the like.

Referring to FIG. 1, the biochemical information detection system 1000 of the present invention includes an imaging unit 101, a white balancing unit 103, a detection area dividing unit 104, a potential color extracting unit 105, a data converting unit 106, an analyzing unit 107, a communicating unit 108, a display 110, and a database 111. This embodiment of the present invention describes that the analyzing unit 107 is implemented in a biochemical analysis server 900 and the other units except the analyzing unit 107 are implemented in the user terminal 100. However, it is noted that the person having ordinary skill in the art can implement some of the above elements selectively in the user terminal 100 or the biochemical analysis server 900 considering appropriate resource allocation. This will be described in detail below with reference to FIGS. 10 and 11.

The user terminal 100 (also referred to as a "biochemical sample diagnosis device" or a "self-diagnosis device") may be understood as a concept encompassing a software or hardware component such as a terminal or application program that is installed in various types of terminals, is capable of transmitting or receiving data to or from the biochemical analysis server 900 as a client, and is capable of transmitting or receiving biochemical information detection-related data.

For example, the user terminal 100 may include various types of portable terminals such as a smartphone, a smart watch, a tablet PC, a digital broadcasting terminal, a personal digital assistant (PDA), and a portable multimedia player (PMP) and may include stationary terminals such as a notebook, a desktop, and the like. However, it is noted that the user terminal 100 is implemented as any terminal capable of transmit or receive biochemical information to or from the biochemical analysis server 900 and display the biochemical information in various ways.

The biochemical analysis server 900 may receive an image of a urine test kit 210 including a biochemical sample rod 220 from the user terminal 100 and that analyzes biochemical information of a pet based on the received image.

The imaging unit 101 may get an image or a video of the biochemical sample rod 220 in the user terminal 100. For example, the imaging unit 101 may include a camera 102.

The camera 102 processes a picture frame of a video or a still image obtained by an image sensor in a photographing mode. The processed image may be displayed on the display 110, or stored in the database 111, which will be described below. The imaging unit 101 may include one or more cameras 102 depending on the form of the terminal.

Figure 5:
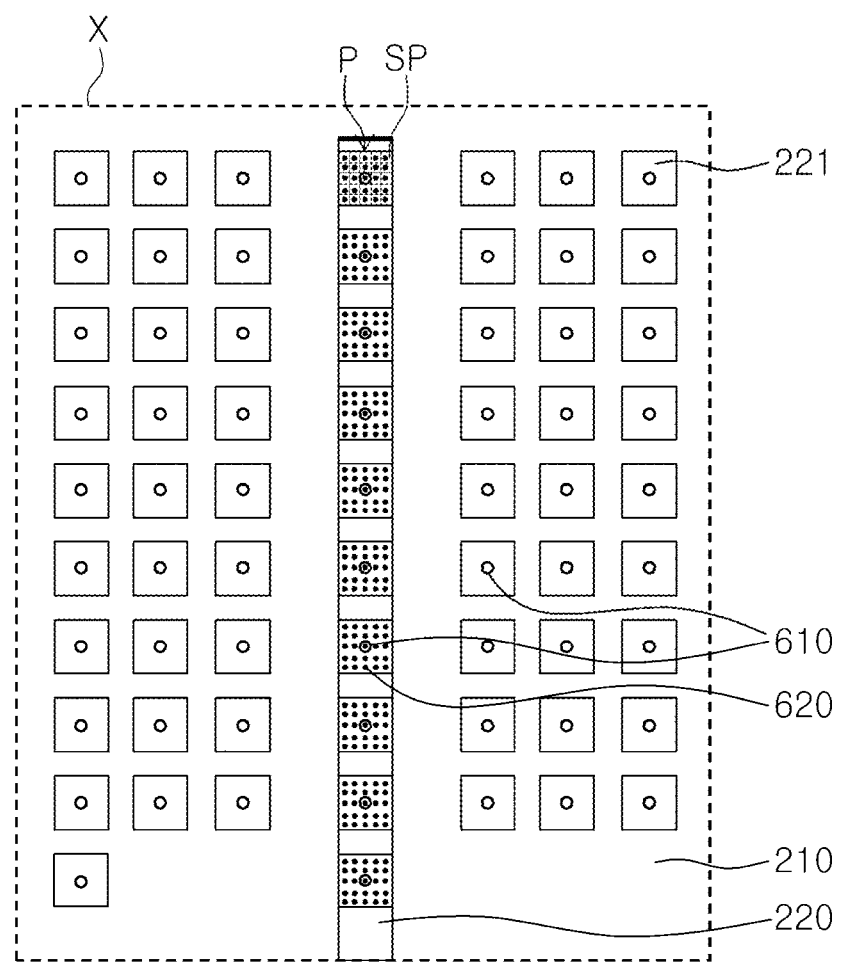
FIG. 5 is an enlarged diagram of an area X of FIG. 2.

The biochemical sample rod 220 refers to a test rod for testing pet urine and includes a plurality of pad cells 211 arranged in a line at regular intervals. For convenience of description, it is assumed in the present invention that there are ten pad cells. Each of the plurality of pad cells 211 attached to the biochemical sample rod 220 may be divided into a plurality of sub-pad cells SP as shown in FIG. 5 which will be described below. Each of the sub-pad cells SP is a square cell. As the size of the sub-pad cell SP decreases, the accuracy of a pet urine test increases.

Figure 2:
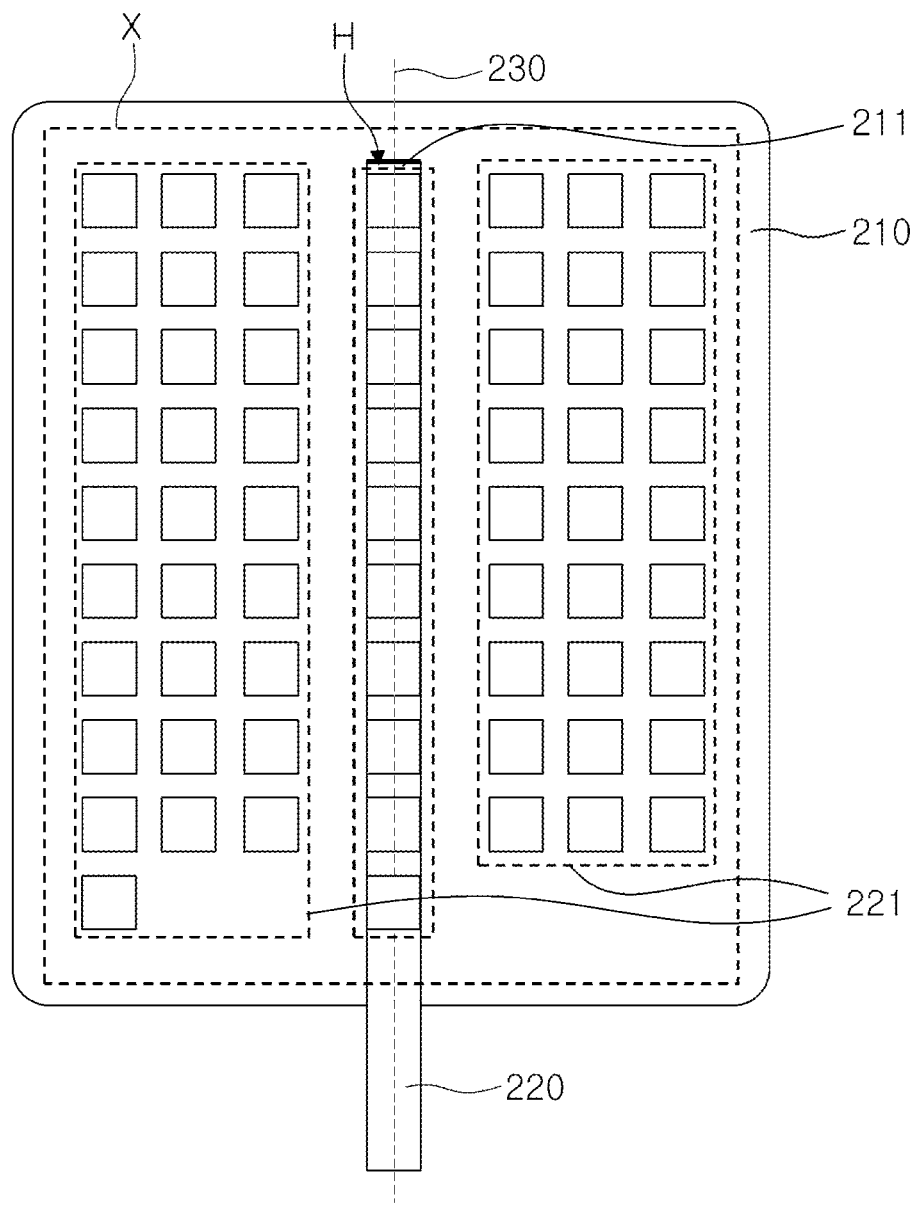
FIG. 2 is an exemplary diagram showing a urine test kit having a biochemical sample rod according to an embodiment of the present invention.

Referring to FIG. 2, the biochemical sample rod 220 may be mounted in a sample rod mounting recess H formed at a center portion of the urine test kit 210. The sample rod mounting recess H is formed to be long in the vertical direction and has a lower surface which is open and an upper surface which is shielded by the urine test kit 210. That is, the sample rod mounting recess H is formed such that a portion of the biochemical sample rod 220 can be inserted into and fixed to an upper end of the sample rod mounting recess H. A plurality of colorimetric table cells 221 are disposed on both sides with respect to the sample rod mounting recess H. In this case, the plurality of colorimetric table cells 221 are arranged in a plurality of rows and columns and are disposed to correspond to the positions of the pad cells 211 formed in the biochemical sample rod 220 to be inserted into the sample rod mounting recess H.

The white balancing unit 103 adjusts the intensities of colors (for example, red, green or blue) in the image acquired by imaging unit. For example, the white balancing unit 103 normalizes the degree of color intensities of a stored image to adjust distortion of colors caused by the ambient environment. In detail, the white balancing unit 103 uses a color constancy algorithm in order to acquire reliable colors during image acquisition regardless of the ambient environment.

Thus, the white balancing unit 103 may convert an input image into normalized color values by correcting a color variation corresponding to the ambient environment by means of the color constancy algorithm and setting the minimal value and the maximal value of an image to be used for analysis.

The ambient environment refers to external factors such as ambient illumination brightness, an illumination color, a camera sensor, etc. during image acquisition. Since a darker image or a brighter image may be acquired depending on the ambient environment, white balancing may be performed by the color constancy algorithm. This will be described in detail below with reference to FIG. 4.

The detection area dividing unit 104 divides an area of a pad cell P included in an acquired image to detect a valid area (hereinafter also referred to as a "detection area"). The valid area refers to an area to be substantially used to detect biochemical information and is included in an area where a color is developed. As shown in FIG. 5, which will be described below, each of the plurality of pad cells 211 attached to the biochemical sample rod 220 may be divided into a plurality of sub-pad cells SP. Each of the sub-pad cells SP is a square cell. As the size of the sub-pad cell SP decreases, the accuracy of a pet urine test increases. For example, the size of the sub-pad cell SP is greater than or equal to about one-tenth of the length of one side of the pad cell P and may be easily changed by those skilled in the art.

In the present invention, basically, the detection area dividing unit 104 may be implemented in the user terminal 100. In some embodiments, the detection area dividing unit 104 may be implemented in the user terminal 100 or the biochemical analysis server 900. This will be described in detail below with reference to FIG. 4.

The potential color extracting unit 105 extracts the colors of the colorimetric table cell 221 and the pad cell P. In this case, the potential colors of the colorimetric table cell 221 and the pad cell P may be extracted in different ways. As the color of the colorimetric table cell 221, an RGB value is acquired from a color extraction point 610 which is marked with "O" at the center of the plurality of colorimetric table cells 221, as shown in FIG. 5. The pad cell P may appear in a color that changes depending on the ingredients of urine, and the colorimetric table cell 221 may appear in a color that changes depending on the surrounding environment such as shadows. However, since the colorimetric table cell 221 appears in a predetermined color and has standard data, it is possible to correct a change in color according to the surrounding environment, and thus the potential color extracted from the center of the colorimetric table cell 221 may be utilized without additional work. However, the potential color may be extracted by means of the same algorithm as that of the pad cell P.

Meanwhile, in the case of the color of the pad cell P, the potential color extracting unit 105 may extract a potential color from a valid area of the pad cell P divided by the detection area dividing unit 104. The potential color may refer to a color that is expressed such that the original features of the color changed by various user environments are distinguishable. Here, the various user environments may include a shadow, reflected light, a color temperature, a camera, an image signal processor of a mobile device, etc. A color with the highest extraction frequency in the valid area except for a leached color or an undeveloped color is defined as the potential color.

The potential color extracting unit 105 may minimize the effects of an undeveloped color or a leached color by using convolution. Here, the undeveloped color refers to a color that is the same as the initial color of the pad cell P because pet urine is not uniformly applied to the pad cell P 211 attached to the biochemical sample rod 220 and thus no color change occurs in the pad cell P. Also, the leached color refers to a color that appears when urine absorbed in any one pad cell P discolors the pad and then contaminates another pad cell.

Alternatively, the potential color extracting unit 105 extracts a potential RGB value by extracting a color having the highest extraction frequency among extracted potential colors. In the present invention, basically, the potential color extracting unit 105 may be implemented in the user terminal 100. In some embodiments, the potential color extracting unit 105 may be implemented in the user terminal 100 or the biochemical analysis server 900. This will be described in detail below with reference to FIG. 4.

The data converting unit 106 is configured to convert an image into a short string of characters or numbers before the image is transmitted to the biochemical analysis server 900 by the communicating unit 108. When the image is transmitted to the biochemical analysis server 900, the image is scaled or resized. In this case, a transmission delay may occur because the resolution of the camera 102 is different for each terminal. That is, the image may be affected by a transmission speed or the like depending on network environments or mobile device performance.

Thus, not by transmitting an image itself to the biochemical analysis server 900 but by converting the image into a short string of characters or numbers, the data converting unit 106 may output a stable result regardless of a network environment (e.g., a network shadow period or a legacy device), that is, while minimizing the dependency on a network environment.

The data converting unit 106 may minimize the date size of the image to about 900 bytes. In the present invention, since an image having image data of array[64][3] is used for convenience of description, the image is converted into a character string having a length of 900 bytes. As a result, when the data size of the image is changed, the length of the character string may be changed. This will be described in detail below. In the present invention, basically, the data converting unit 106 may be implemented in the user terminal 100. In some embodiments, however, the data converting unit 106 may be implemented in the biochemical analysis server 900 or omitted.

Also, the data converting unit 106 may convert a plurality of potential RGB values extracted by the potential color extracting unit 105 into an array corresponding to the number of sample test items. The potential RGB values converted into the array are delivered to the biochemical analysis server 900. Here, the sample test items may refer to ingredient items for diagnosing a suspected disease of a pet. For example, the ingredient items may include glucose, bilirubin, ketone, specific gravity, blood, protein, nitrite, urobilinogen, etc., but the present invention is not limited thereto.

The analyzing unit 107 is configured to convert and analyze a potential RGB value for an image received from the user terminal 100 or the biochemical analysis server 900 using various color spaces.

For example, the various color spaces may include a red, green, and blue (RGB) color space, a hue, saturation, and value (HSV) color space, a hue, saturation, and lightness (HSL) color space, a hue, saturation, and intensity (HSI) color space, a hue, saturation, and brightness (HSB) color space, and a cyan, magenta, yellow, a black (CMYK) color space, etc.

For example, the color space may include any one of RGB, HSV, $c_1c_2c_3$, $\ell_1\ell_2\ell_3$, $m_1m_2m_3$, and, Lab.

The analyzing unit 107 may serve to convert the potential RGB value using various color spaces and to find a color that most closely matches a color developed from each of the color spaces. Also, the analyzing unit 107 includes a color space conversion engine for color space conversion (hereinafter referred to as a first engine) and a color space analysis engine for color space analysis (hereinafter referred to as a second engine). This will be described in detail below.

The communicating unit 108 is an element for communicating with the biochemical analysis server 900 or other terminals through a network. For example, the communicating unit 108 may include Bluetooth, Zigbee, Wireless Local Area Network (WLAN), Long Term Evolution (LTE), etc.

The display 110 is an element configured to display and output various information processed by the user terminal 100 or the biochemical analysis server 900 or various information received from the biochemical analysis server 900. For example, the display 110 may display a guide screen used for the user terminal 100 to recognize a urine test kit, display an image captured by the camera 102, and display biochemical information analyzed by the user terminal 100 or the biochemical analysis server 900 on the basis of the above-described image.

The database 111 may store other information and data necessary to implement the biochemical analysis method of the present invention, a plurality of pieces of biomedical analysis information transmitted from the biochemical analysis server 900, etc.

A process of performing a biochemical sample test according to an embodiment of the present invention will be described below with reference to FIGS. 3 to 7.

Figure 3:
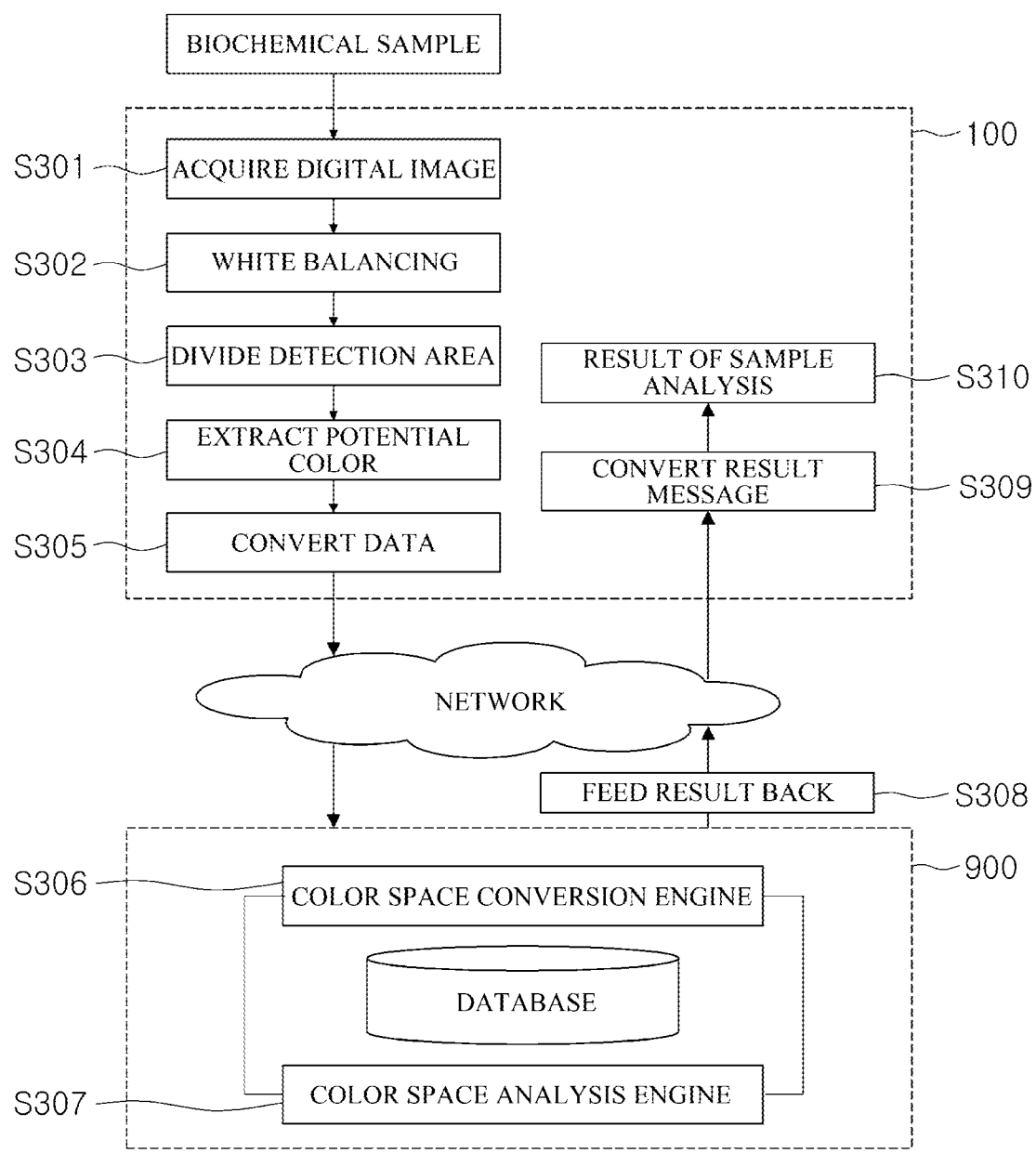
FIG. 3 is an exemplary diagram showing a process of operating a biochemical sample test in an environment in which a local and a server are combined according to an embodiment of the present invention.
Figure 4:
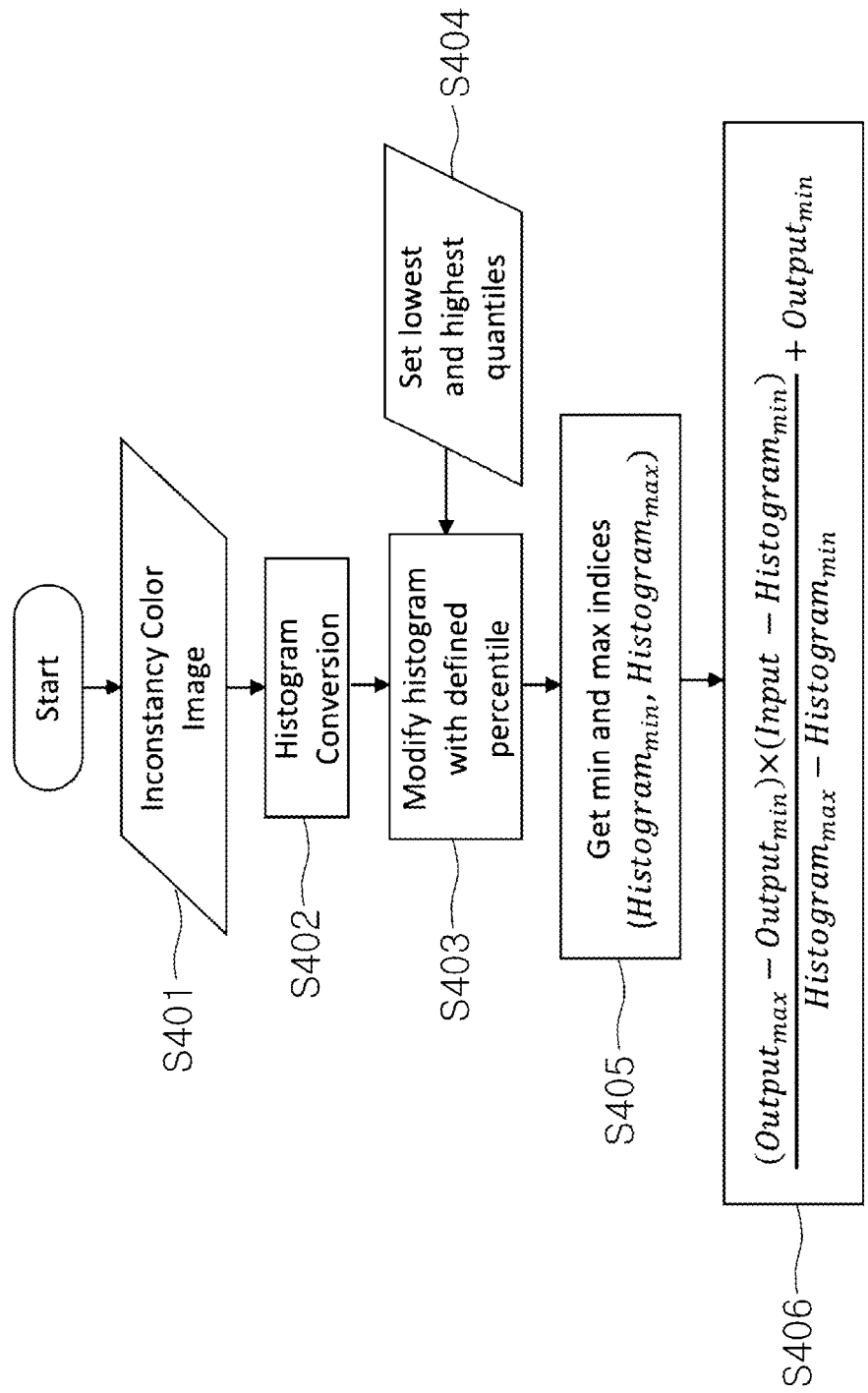
FIG. 4 is a flowchart illustrating a color constancy algorithm according to an embodiment of the present invention.
Figure 6:
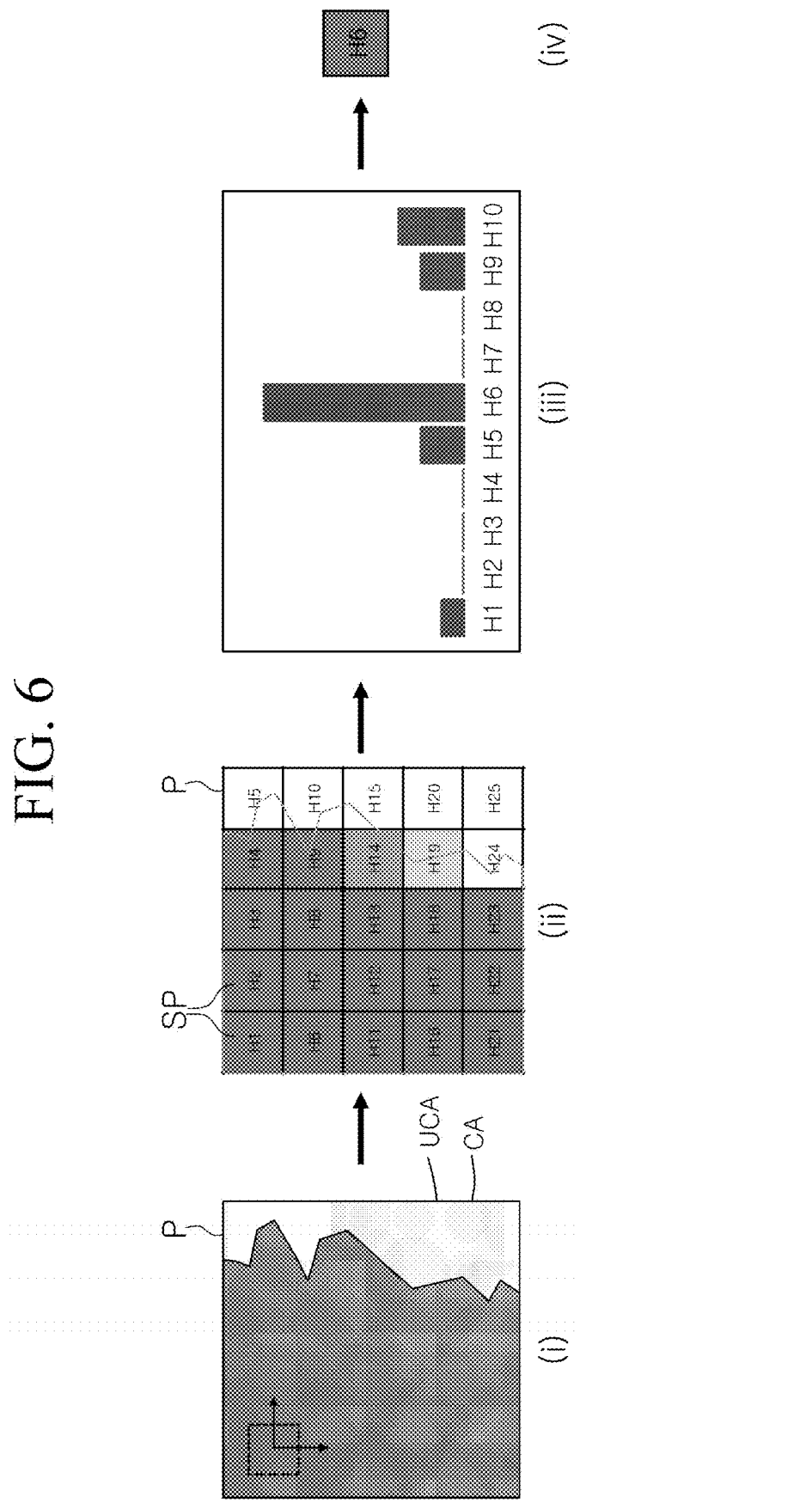
FIG. 6 is an exemplary diagram illustrating a process of dividing a detection area and extracting a potential color using convolution according to an embodiment of the present invention.
Figure 7:
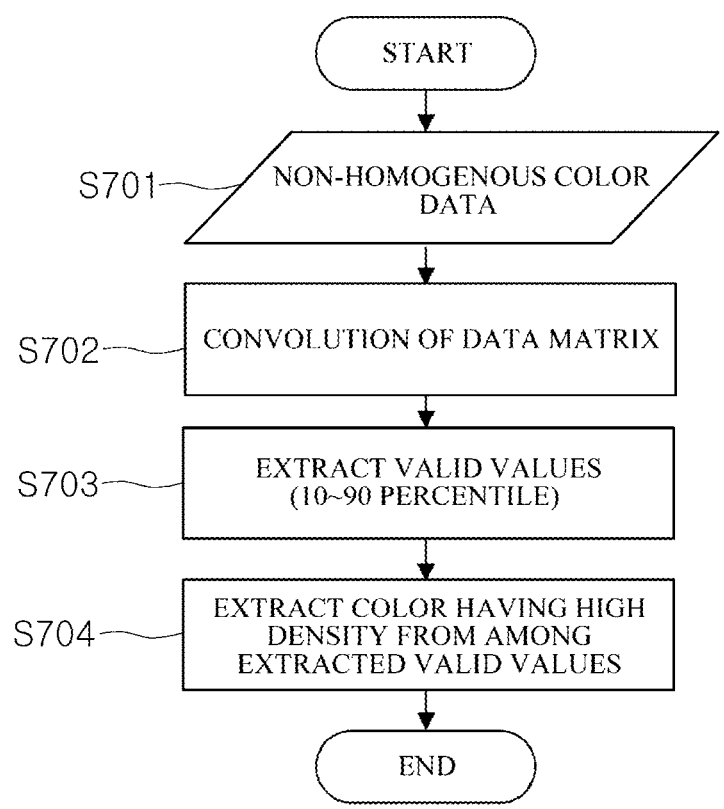
FIG. 7 is a flowchart illustrating a data conversion process according to an embodiment of the present invention.

FIG. 3 is an exemplary diagram showing a process of operating a biochemical sample test in an environment in which a local and a server are combined according to an embodiment of the present invention. FIG. 4 is a flowchart illustrating a color constancy algorithm according to an embodiment of the present invention. FIG. 5 is an enlarged diagram of an area X of FIG. 1. FIG. 6 is an exemplary diagram illustrating a process of dividing a detection area and extracting a potential color using convolution according to an embodiment of the present invention. FIG. 7 is a flowchart illustrating a data conversion process according to an embodiment of the present invention.

Referring to FIG. 3, the imaging unit 101, the white balancing unit 103, the detection area dividing unit 104, the potential color extracting unit 105, the data converting unit 106, and the display 110 may be implemented in software, hardware, or a combination of software and hardware in the user terminal 100. Also, the analyzing unit 107 may be a module that is implemented in the biochemical analysis server 900 and implemented in software, hardware, or a combination of software and hardware.

Image Acquisition and White Balancing

The imaging unit 101 acquires an image or video for the biochemical sample rod 220 from the camera 102 of the user terminal 100 (S301). In this case, the acquired image or video is stored in a memory, and the stored image is white-balanced by the white balancing unit 103 (S302). The white balancing unit 103 may increase color development using a color constancy algorithm in order to minimize a variation caused by a surrounding environment.

Color Constancy Algorithm

First, an image having an inconstant color value that is not white-balanced is input (S401), and the input image is normalized and converted into a histogram (S402). Subsequently, the histogram is reconverted to be divided into a predetermined minimal displacement value and maximal displacement value (S403), and the minimal rank value $Histogram_{min}$ and the maximal rank value $Histogram_{max}$ value are extracted from the reconverted histogram (S405). In this case, an image (or video) having a constant color value may be implemented by using the extracted rank value and the predetermined minimal displacement value and maximal displacement value, as shown in Equation 1 below:

$$\frac{(Output_{max} - Output_{min}) \times (Input - Histogram_{min})}{Histogram_{max} - Histogram_{min}} + Output_{min}$$

[Equation 1]

where $Output_{max}$ indicates an extracted maximal displacement value, $Output_{min}$ indicates an extracted minimal displacement value, Input indicates an input value, $Histogram_{min}$ indicates a minimal histogram rank, and $Histogram_{max}$ indicates a maximal histogram rank.

Detection Area Division Process

The detection area dividing unit 104 divides a detection area of an image white-balanced by the above-described color constancy algorithm (S303).

The pad cell P is an area that is substantially analyzed when pet urine is tested using the biochemical sample rod and has a color value with a constant color distribution due to the color constancy algorithm. Also, the pad cell P includes a plurality of sub-pad cells SP divided into a plurality of cells in the form of a checkerboard as shown in FIG. 5. The pad cell P may be divided into a valid area CA where a color is developed in only some areas and an invalid area UCA where no color is developed. In detail, in order to test pet urine, it is preferable that the urine is uniformly absorbed in the entire area of the pad cell P. However, the urine and the pad are not uniformly brought into contact with each other, and thus a color shown in (i) of FIG. 6 may be developed.

When the pad cell P where a color is not uniformly developed is divided as shown in (ii) of FIG. 6, a plurality of 25 sub-pad cells H1, H2, ..., H25 may be generated. As shown in (ii), when a dark color is displayed in the sub-pad cell SP, the sub-pad cell SP may be classified as a valid area where a color is developed, and when the sub-pad cell SP is not painted or lightly painted, the sub-pad cell SP may be classified as an invalid area where no color is developed. That is, the valid area may include H1, H2, H3, H4, H6, H7, H8, H9, H11, H12, H13, H16, H17, H18, H21, H22, and H23, and the invalid area may include areas other than the valid areas. Meanwhile, in (ii) of FIG. 6, the pad cell P is divided in five columns and five rows, but when the pad cell P is divided into more than five columns and more than five rows, the valid areas may be classified more accurately. That is, according to the present invention, it is possible to improve the accuracy of analysis by classifying a plurality of valid areas.

Potential Color Extraction and Data Conversion Process

The potential color extracting unit 105 performs an operation of extracting a potential color in a first color space from an image prepared in this way. For example, the first color space is an RGB color space, and thus, for convenience, the following description assumes that the first color space is an RGB color space. That is, the first color space may include several different color spaces.

In detail, the potential color extracting unit 105 extracts a potential color from valid areas of the pad cell P and the colorimetric table cell 221 (S304). Subsequently, the data converting unit 106 converts extracted potential RGB values into an array and delivers the potential RGB values to the biochemical analysis server 900 through a network (S305). Here, any one of the potential RGB values converted into the array by the data converting unit 106 may be expressed by eight bits corresponding to variables R, G, and B.

Also, the potential color extracting unit 105 extracts an RGB value from a center portion of the colorimetric table cell 221. Also, the potential color extracting unit 105 may extract a color having the highest extraction frequency after using convolution in a plurality of valid areas obtained by dividing the pad cell P using the above-described method. Here, the color having the highest extraction frequency is a potential color of the pad cell, and it is preferable that a unique RGB value of the potential color of the pad cell is understood as a potential RGB value.

In detail, referring to FIG. 5, color extraction points 610 are located at the central points of the plurality of pad cells P and the plurality of colorimetric table cells 221 included in the urine test kit 210. The color extraction points 610 marked with "0" at the central points of the plurality of pad cell P and the plurality of colorimetric table cells 221 are points for acquiring RGB values of the central points of the pad cells P and the colorimetric table cells 221.

Thus, referring to FIG. 5, a total number of color extraction points 610 located in the plurality of colorimetric table cells 221 arranged in nine rows and six columns (9×6) is 54, but the present invention is not limited thereto. The plurality of color extraction points 610 have unique intensities. As shown in FIG. 7, the data converting unit 106 may convert the intensities of the color extraction points 610 included in the plurality of colorimetric table cells 221 into an array and may store the array in array[54][3]. In the present invention, for convenience of description, a 54×3 array is used because a three-channel environment is used as an example. However, when the dimension of the color space is changed or the number of colorimetric tables is changed, the numbers of rows and columns of the array may be changed.

Subsequently, convolution is performed on the values R, G, and B of convolution points 620 included in the plurality of sub-pad cells SP, and then a result of the convolution is stored in array[10][3]. In detail, a plurality of convolution points 620 are formed around a color extraction point 610 located at the center point of a pad cell attached to the biochemical sample rod 220. In the present invention, for convenience of description, a 10×3 array is used because ten pad cells P are used as an example. However, when the number of pad cells is changed, the numbers of rows and columns of the array may be changed.

As shown in FIG. 5, 25 convolution points 620 are included in the pad cell P, and each of the convolution points 620 has a unique intensity (hereinafter referred to as (r, g, b)). Thus, the intensities of the 25 convolution points 620 included in one pad cell P may be converted into one RGB coordinate value through convolution.

In this regard, the convolution may be performed by applying convolution filter having the form of a 5×5 matrix to the 25 convolution points 620. As shown in Equation 2 below, feature values having unique intensities may be calculated using a Gaussian filter.

In this case, several feature points corresponding to the number of convolution points are generated, and the feature points may include $B_{11}$ to $B_{55}$ as disclosed in Equation 2 below. $B_{11}$ may have a unique intensity $(r_{11}, g_{11}, b_{11})$, $B_{15}$ may have a unique intensity $(r_{15}, g_{15}, b_{15})$, $B_{51}$ may have a unique intensity $(r_{51}, g_{51}, b_{51})$, and $B_{55}$ may have a unique intensity $(r_{55}, g_{55}, b_{55})$. Meanwhile, in the present invention, the convolution filter is not limited thereto, and any filter that can compensate for data loss may be used as the convolution filter.

$$\begin{pmatrix} A_{11} & \cdots & A_{15} \\ \vdots & \ddots & \vdots \\ A_{51} & \cdots & A_{55} \end{pmatrix} * (\text{Gaussian filter}) \rightarrow \begin{pmatrix} B_{11} & \cdots & B_{15} \\ \vdots & \ddots & \vdots \\ B_{51} & \cdots & B_{55} \end{pmatrix} \quad \text{[Equation 2]}$$

Thus, valid values are extracted from among feature values having passed through the Gaussian filter (S703), and a color having the highest density is extracted from among the extracted valid values as a potential RGB value (S704).

In other words, a color having high density may be extracted from among several colors developed in one pad cell P as a final valid value (hereinafter referred to as a "potential RGB value"). Here, it is preferable that the value having the high density is understood as the degree to which the developed color is dark. For example, when red is developed in an uppermost area of one pad cell P and light red is developed in the remaining area other than the uppermost area, the potential color extracting unit 105 may extract, as a valid value, an uppermost area where a dense color is developed.

Operation S703 and S704 will be described in detail below. The biochemical sample rod 220 having ten pad cells P has ten potential RGB values and thus may perform array conversion on the potential RGB values and store the values in array[10][3].

Thus, array[64][3] is obtained by summing array[54][3] and array[10][3] stored through the array conversion in S701 and S702 and finally delivered to the biochemical analysis server 900. In this case, array[64][3] functions as a potential RGB value.

In relation to the convolution, a conventional urine test kit sets a central area of the pad cell P attached to the test rod as the center of the moment. However, since the remaining area of the pad cell P other than the central area is discolored, the test cannot be performed. Accordingly, disadvantageously, a large amount of sampling is required. In addition, conventionally, averaging is also used for the sampling. However, in this case, the maximal and minimal values are modified disadvantageously. In other words, since averaging decreases the maximal value and increases the minimal value, the valid values in the plurality of valid areas lose their respective characteristics. Also, in a conventional case, a minimal-maximal value (Min-max) is obtained in one dimension, and then sampling may be performed. However, progression in multiple dimensions is not possible.

In contrast, according to the present invention, a detection area is divided for one of a plurality of pad cells P attached to a biochemical sample rod 220, and then convolution is performed on a plurality of sub-pad cells SP obtained through division. Thus, according to the present invention, the characteristics (potential RGB values) of each of the sub-pad cells SP may be combined without removal or modification.

Also, according to the present invention, a valid value is detected from a three-dimensional (3D) color space environment, and thus it is difficult to detect the minimal-maximal value (Min-max) due to the characteristics of the 3D space. However, effective sampling is possible because convolution is performed instead of averaging, unlike the conventional art.

Subsequently, two engines included in the biochemical analysis server 900 convert and analyze at least one potential RGB value received from the user terminal 100 by using a plurality of color spaces (S306, S307) and deliver an analysis result feedback to the user terminal 100 (S308). The biochemical analysis server 900 converts a potential color in an RGB color space into a color value in another color space and then selects a colorimetric table cell having the closest color to any one of the plurality of pad cells from among a plurality of colorimetric table cells in the color space on the basis of the converted color value.

In detail, the two engines included in the biochemical analysis server 900 include a color space conversion engine and a color space analysis engine, as shown in FIG. 3. The color space conversion engine may convert a received potential RGB value into color values in various other color spaces. For example, when R, G, and B are converted into $\ell_1\ell_2\ell_3$, $\ell_1\ell_2\ell_3$ may be calculated using Equation 3 below:

$$\ell_1 = \frac{(R-G)^2}{(R-G)^2 + (R-B)^2 + (G-B)^2} \quad \text{[Equation 3]}$$

$$\ell_2 = \frac{(R-G)^2}{(R-G)^2 + (R-B)^2 + (G-B)^2}$$

$$\ell_3 = \frac{(G-B)^2}{(R-G)^2 + (R-B)^2 + (G-B)^2}$$

As described above, by extracting values detected and classified from various color spaces, a color that most closely matches a color developed in the pad cell P is detected. In this case, it is preferable that the most closely matching color is understood to mean a color having a color coordinate value of a color space closest to the coordinate value of the developed color. For example, it is assumed that the coordinate value of the developed color is (3, 1, 5). When the coordinate value of the first color space is (3, 1, 3) and the coordinate value of the second color space is (3, 1, 2), it may be determined that the developed color is a color in a coordinate (3, 1, 2) of the second color space.

Subsequently, the user terminal 100 converts a result feedback delivered from the biochemical analysis server 900 into a message (S309) and then outputs an analysis result for a pet's biochemical information through the display 110 (S310).

The structure and process of a dynamic random node tree will be described in detail below with reference to FIGS. 8A, 8B and 9.

Figure 8A:
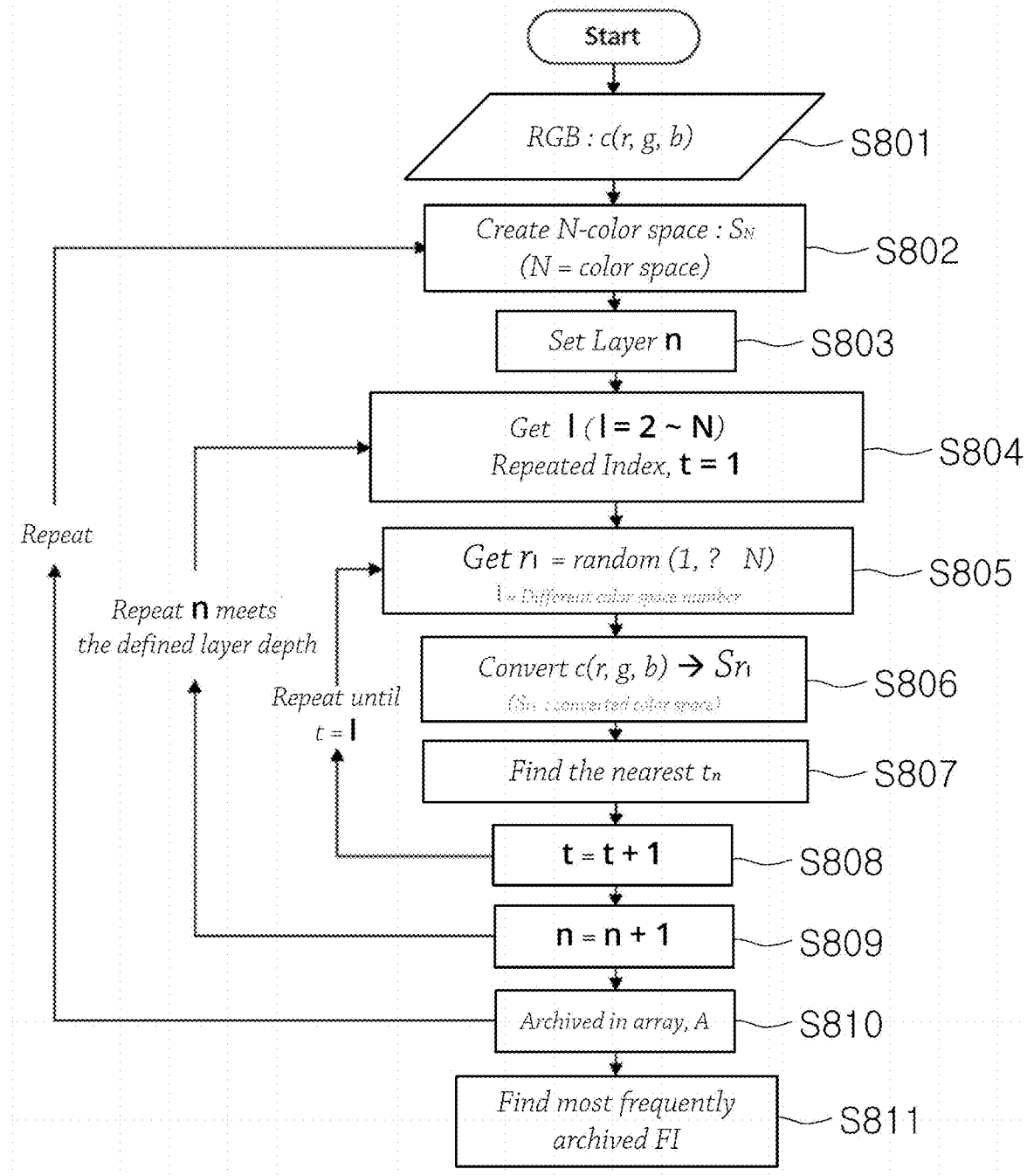
FIG. 8A is a flowchart illustrating a process of operating a dynamic random node tree according to an embodiment of the present invention.

FIG. 8A is a flowchart illustrating a process of operating the dynamic random node tree according to an embodiment of the present invention. FIG. 8B is an exemplary diagram illustrating the structure of the dynamic random node tree in detail. FIG. 9 is an exemplary diagram showing a process of repeating a process of voting for a predicted value using the dynamic random node tree according to an embodiment of the present invention.

Figure 8B:
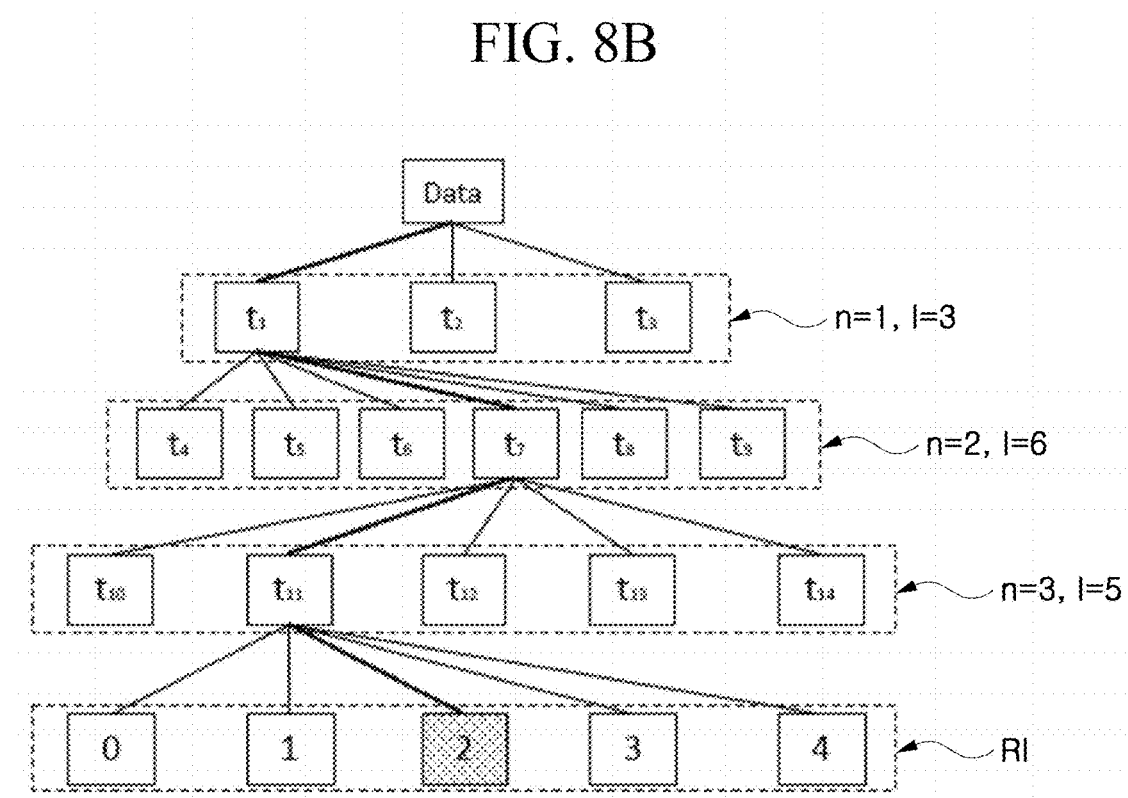
FIG. 8B is an exemplary diagram illustrating the structure of the dynamic random node tree in detail.

Referring to FIGS. 8A and 8B, a potential RGB value (e.g., c(r, g, b)) extracted by the potential color extracting unit is received (S801).

Subsequently, N color spaces SN are generated (S802). Here, N indicates the total number of colors used in the dynamic random node tree.

Subsequently, n layers in which all the color spaces are to be randomly arranged are set (S803). In this case, the number of layers is fixed in the dynamic random node tree, and basically the dynamic random node tree starts from the first layer. For example, as shown in FIGS. 8A and 8B, the layers of all the color spaces may be set as n=3.

Subsequently, $\ell$ color spaces are extracted (S804). Here, $\ell$ indicates a color space, and at least two color spaces are included in one layer. In particular, $\ell$ color spaces included in one layer are of different types. However, color spaces included in different layers may be of the same or different types.

Also, a different number of color spaces may be included for each layer. For example, as shown in FIG. 8B, a layer corresponding to n=1 is $\ell$=3, that is, three color spaces $t_1$, $t_2$, and $t_3$ are included, a layer corresponding to n=2 is $\ell$=6, that is, six color spaces $t_4$, $t_5$, $t_6$, $t_7$, $t_8$, and $t_9$ are included, a layer corresponding to n=3 is $\ell$=5, that is, five colors $t_{10}$, $t_{11}$, $t_{12}$, $t_{13}$, and $t_{14}$ are included.

Subsequently, color spaces to be arranged in a layer are randomly extracted from the extracted color spaces (S805). In the present invention, the randomly extracted color space is defined as $r_1$.

Subsequently, Data, which is a potential RGB value, is converted using the randomly extracted color space $r_1$ (S806). In the present invention, the color space converted by the randomly extracted color space is defined to be Sri.

Subsequently, a color space to having a distance value closest to the input data is selected from the color spaces that are randomly selected for the layers (S807).

Subsequently, operations S805 to S807 are repeated while increasing the order number of the color space that is randomly selected for one of the plurality of layers one at a time (t=t+1) (S809). In this case, the order number of the color space is increased by the number $\ell$ of color spaces included in a layer where the corresponding color space is located (Repeat unit t=$\ell$).

Here, after a process for operation S809 is completed in one layer, operations S804 to S808 are repeated while increasing the order number one at a time in the next layer (n=n+1). In this case, the order number of the layer is increased until the order number reaches a predetermined number of layers (Repeat n meets the defined layer depth).

Thus, a predicted value having the closest distance value may be voted for by using the randomly extracted color space (S810) and, by iterating a process of finding the predicted value (or "Result Index") having the closest distance value to first input data, the most voted predicted value RI may be extracted as a final predicted value (or as a "final index FI") (S811).

Figure 9:
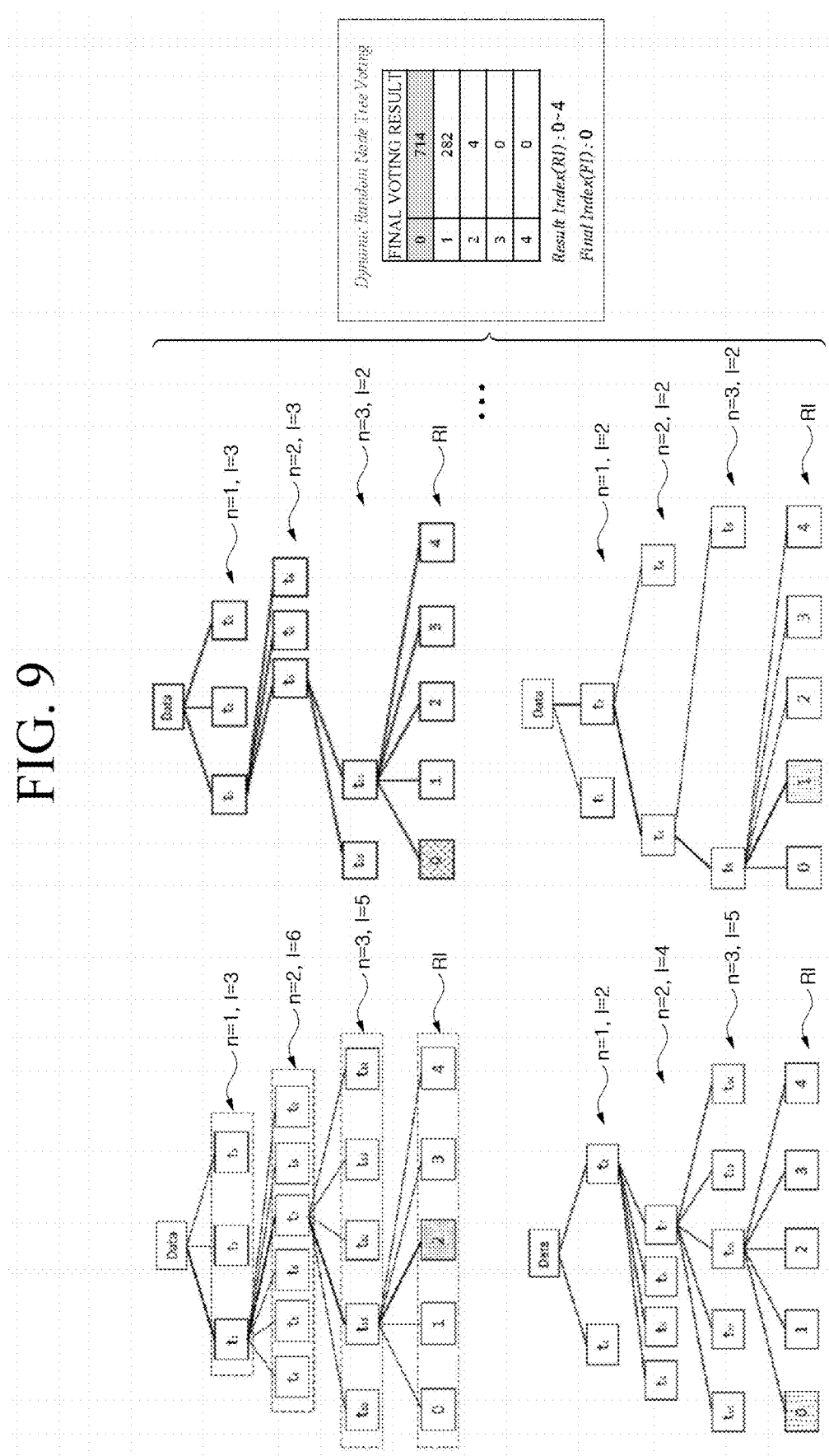
FIG. 9 is an exemplary diagram showing a process of repeating a process of voting for a predicted value using the dynamic random node tree according to an embodiment of the present invention.

In this case, a process of voting for the predicted value RI in order to extract the final predicted value FI may be repeated (Repeat) as shown in FIG. 9. In detail, referring to FIG. 9, by repeating operations S801 to S811, it can be seen that 0, 1, and 2 are predicted to be predicted values RI, and 0 is most voted for among the predicted values RI. Accordingly, 0 may be extracted as the final predicted value FI.

Accordingly, by dividing the area of a pad to be tested and extracting R, G, and B through convolution, the biochemical information detection system 1000 according to an embodiment of the present invention can derive an accurate result even when only some of the pad cell P is discolored.

Also, by applying a color constancy algorithm, the biochemical information detection system 1000 according to an embodiment of the present invention can derive a certain result value regardless of ambient environments.

Also, by repeatedly predicting a result index using a dynamic random node tree and outputting a final index on the basis of extraction frequencies of a plurality of predicted result values, the biochemical information detection system 1000 according to an embodiment of the present invention can derive a reliable result regardless of ambient environments.

Also, by performing a reliable real-time test using minimal resources, the biochemical information detection system 1000 according to an embodiment of the present invention can effectively improve market competitiveness.

Figure 10:
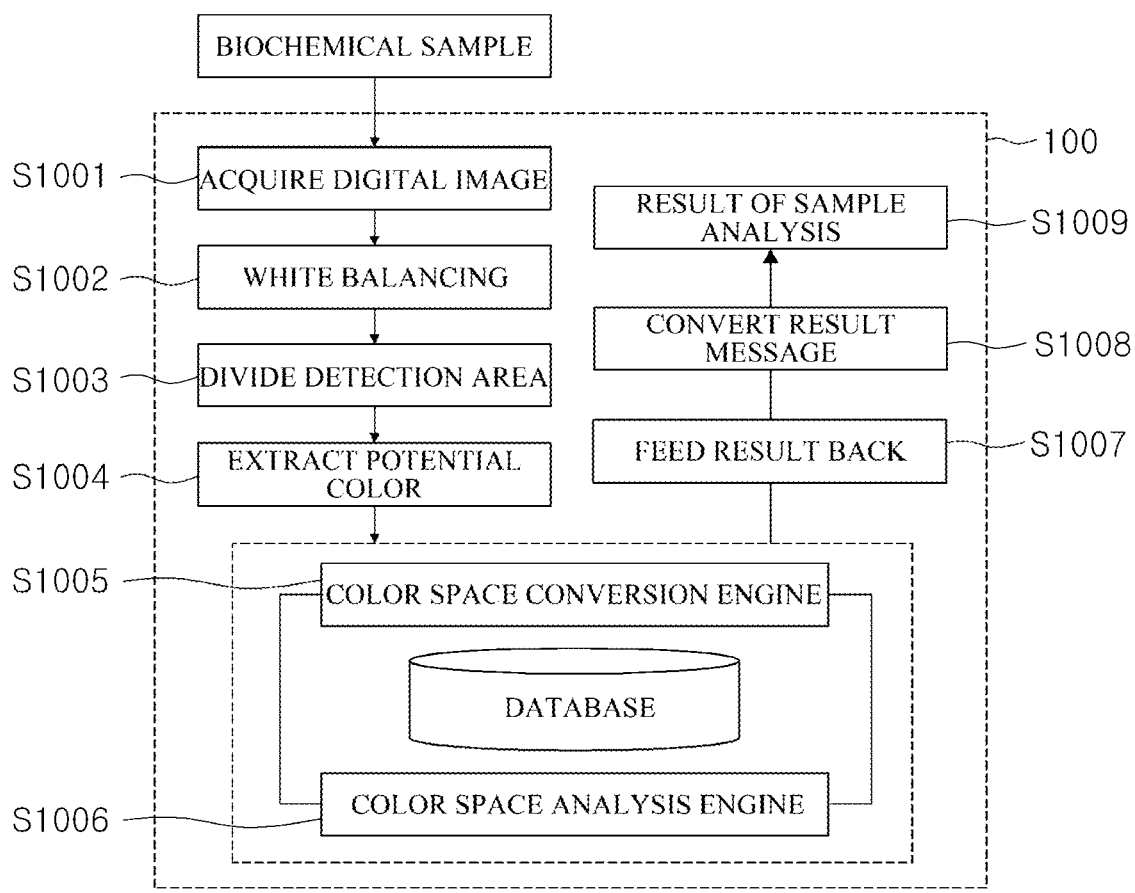
FIG. 10 is a flowchart showing a process of operating a biochemical sample test dependent on a local environment according to an embodiment of the present invention.

FIG. 10 is a flowchart showing a process of operating a biochemical sample test dependent on a local environment according to another embodiment of the present invention.

In the biochemical information detection system 1000 according to another embodiment of the present invention, processors are operated in only the user terminal 100. In detail, as shown in FIG. 10, all of the imaging unit 101, the white balancing unit 103, the detection area dividing unit 104, the potential color extracting unit 105, the analyzing unit 107, and the display 110 are operated in the user terminals 100.

Accordingly, the biochemical information detection system according to another embodiment of the present invention can derive a stable result in a network environment in which an image or a video is difficult to transmit or receive because processors are operated in only the user terminal 100.

Also, by allowing all the processors to locally perform processing, the biochemical information detection system according to another embodiment of the present invention can omit an unnecessary data transmission process and thus improve a work speed.

Figure 11:
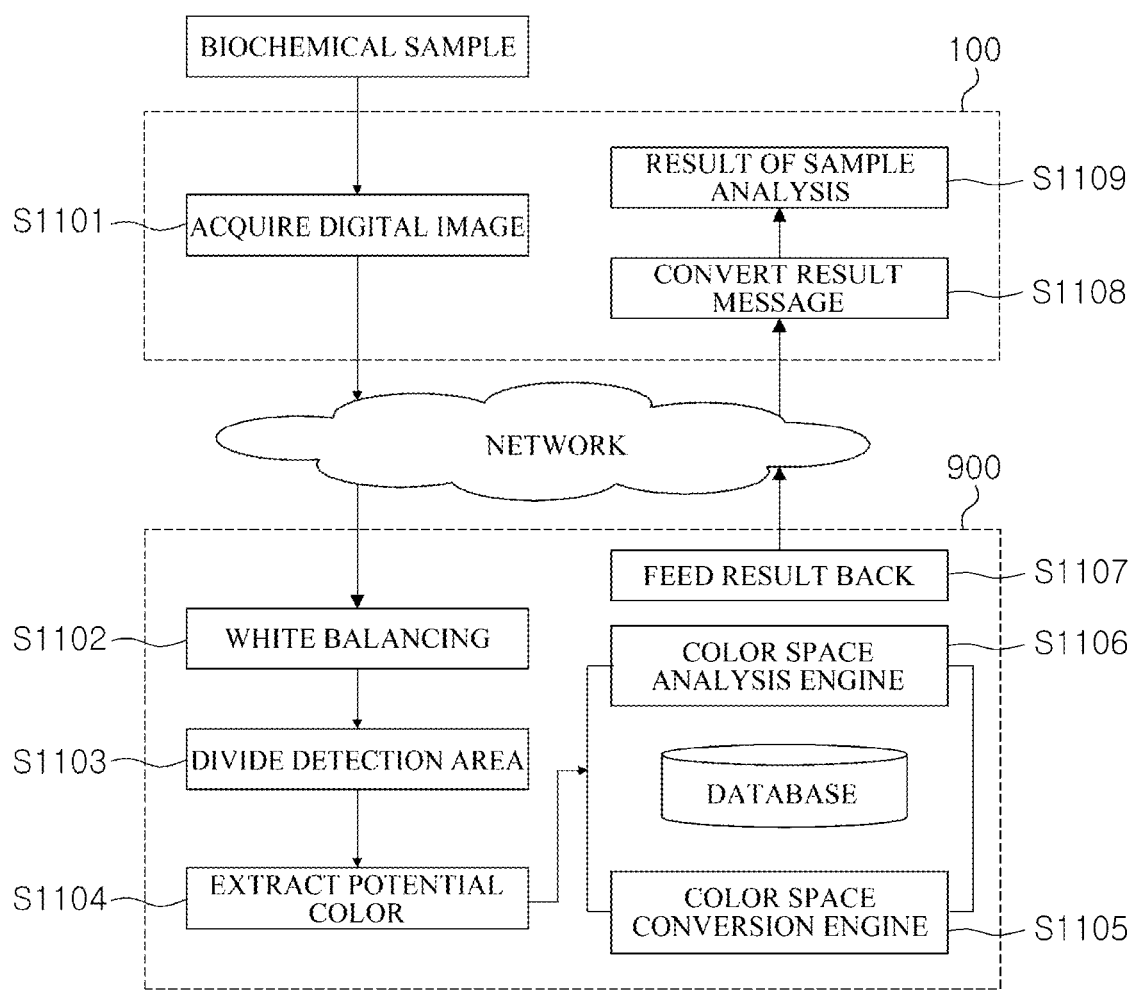
FIG. 11 is a flowchart showing a process of operating a biochemical sample test dependent on a server environment according to an embodiment of the present invention.

FIG. 11 is a flowchart showing a process of operating a biochemical sample test dependent on a server environment according to still another embodiment of the present invention.

In the biochemical information detection system 1000 according to still another embodiment of the present invention, only a minimal number of processors are operated in a user terminal, and all the other processors are operated in the biochemical analysis server 900. As shown in FIG. 11, the imaging unit 101 and the displays 110 are operated in the user terminal 100, and the white balancing unit 103, the detection area dividing unit 104, the potential color extracting unit 105, and the analyzing unit 107 are operated in the biochemical analysis server 900.

Accordingly, by operating only a minimal number of processors in the user terminal 100 and operating the other processors on the analysis side, the biochemical information detection system 1000 according to still another embodiment of the present invention can minimize the amount of data to be processed in the user terminal 100 and maximize the work speed.

Also, by operating processors only on an analysis side, the biochemical information detection system 1000 according to still another embodiment of the present invention can obtain a result at the same rate regardless of the form of the user terminal 100.

It is possible to detect an accurate color by introducing artificial-intelligence-based color space conversion into a urine test reference color sheet and test pad in which a distorted color appears unless the urine test reference color sheet and test pad is in an ideal environment when an image sensor is used for imaging.

Also, according to the present invention, it is possible to derive an accurate result even when only some pad cells are discolored by calculating representative R, G, and B values that have no distortion even without the entire color data of a desired area through convolution of a color of a reference area and a color of a divided test pad area.

Also, according to the present invention, it is possible to derive a certain result value regardless of ambient environments by applying a color constancy algorithm.

Also, according to the present invention, it is possible to derive a result value with significantly enhanced accuracy by applying a dynamic random node tree to various color space conversions to repeatedly predict a result index and by deriving a final index on the basis of an extraction frequency from among a plurality of predicted result values.

Also, according to the present invention, it is possible to effectively improve market competitiveness by performing a reliable real-time test using minimal resources.

Advantageous effects of the present invention are not limited to the above-description, and various other effects are included in this specification.

A computer according to the present invention typically includes various computer-readable media. Any medium accessible by a computer may be a computer-readable medium, and the computer-readable medium may include volatile and nonvolatile media, transitory and non-transitory media, and mobile and non-mobile media. The present invention is not limited thereto, and the computer-readable recording medium may include computer-readable storage media and computer-readable transmission media.

The computer-readable recording media includes volatile and non-volatile media, transitory and non-transitory media, and the mobile and non-mobile media that are implemented in any method or technique for storing information such as computer-readable instructions, data structures, program modules or other data. The computer-readable storage media may include a random-access memory (RAM), a read-only memory (ROM), an electrically erasable programmable ROM (EEPROM), a flash memory, or other memory techniques, a compact disc ROM (CD-ROM), a digital versatile disc (DVD), or other magnetic storage devices, or any other media that may be accessed by a computer and used to store desired information, but the present invention is not limited thereto.

Computer-readable recording media typically embody computer-readable instructions, data structures, program modules or other data on modulated data signals such as carrier waves or other transmission mechanism and include any information delivery media. The term "modulated data signal" means a signal having one or more characteristics that are set or changed to encode information in the signal. By way of example and not limitation, computer-readable transmission media include wired media such as a wired network or a direct-wired connection and wireless media such as a sound, a radio frequency (RF), infrared light, or other wireless media. Any combinations of the above-described media are also included within the scope of the computer-readable transmission media.

The various embodiments presented herein may be embodied as a method, apparatus, or a manufactured article that uses standard programming and/or engineering techniques. The term "manufactured article" includes computer programs, carriers, or media accessible from any computer-readable apparatus. For example, the computer-readable storage media include magnetic storage devices (e.g., a hard disk, a floppy disk, a magnetic strip, etc.), optical disks (e.g., a CD, a DVD, etc.), smart cards, and flash memory devices (e.g., an EEPROM, a card, a stick, a key drive, etc.), but the present invention is not limited thereto.

It is understood that the specific order or hierarchy of the operations included in the presented processors is an example of exemplary approaches. Based upon design priorities, it is understood that the specific order or hierarchy of the operations in the processes may be rearranged within the scope of the present invention.

While the embodiments of the present invention have been described in detail above with reference to the accompanying drawings, the present invention is not limited to the embodiments, and various changes and modifications may be made without departing from the technical spirit of the present invention. Accordingly, the embodiments disclosed herein are to be considered descriptive and not restrictive of the technical spirit of the present invention, and the scope of the technical spirit of the present invention is not limited by the embodiments. Therefore, it should be understood that the above embodiments are illustrative rather than restrictive in all respects. The scope of the invention should be construed by the appended claims, and all technical spirits within the scopes of their equivalents should be construed as being included in the scope of the invention.

What is claimed is:

1. A method of measuring biochemical information using color space conversion, the method comprising:
acquiring an image of a urine test kit equipped with a biochemical sample rod including a pad cell, the urine test kit including a plurality of colorimetric table cells;
extracting a potential color of a first color space of the plurality of colorimetric table cells and the pad cell from the image;
extracting the potential color as a color of a color space other than the first color space;
selecting a colorimetric table cell having a color closest to any one of a plurality of pad cells of the other color space from among a plurality of colorimetric table cells; and
diagnosing urine by determining a result index on the basis of a colorimetric table cell index having a color closest in the color space other than the first color space,
wherein the extracting of the potential color of the first color space comprises:
generating a color matrix from the color of the first color space extracted from a plurality of color extraction points included in the pad cell; and
extracting a potential color of each of the plurality of pad cells on the basis of a convolution value of the color matrix and a convolution filter.

2. A method of measuring biochemical information using color space conversion, the method comprising:
acquiring an image of a urine test kit equipped with a biochemical sample rod including a pad cell, the urine test kit including a plurality of colorimetric table cells;
extracting a potential color of a first color space of the plurality of colorimetric table cells and the pad cell from the image;
extracting the potential color as a color of a color space other than the first color space;
selecting a colorimetric table cell having a color closest to any one of a plurality of pad cells of the other color space from among a plurality of colorimetric table cells;
diagnosing urine by determining a result index on the basis of a colorimetric table cell index having a color closest in the color space other than the first color space;
extracting the potential color of the first color space as colors of the second to $\ell$ th color spaces in the case of an integer $\ell$ of three or more;
finding $t^{th}$ color distances between a colorimetric table cell having a color closest in the $t^{th}$ color spaces, where $2 \leq t \leq \ell$, and colors obtained by converting the color of the pad cell into the colors of the $t^{th}$ color spaces and selecting a color space having the smallest color distance among the $t^{th}$ color distances; and
determining a colorimetric table cell index having a color closest in the selected color space as the result index when the urine is diagnosed by determining the result index on the basis of the colorimetric table cell index having the color closest in the other color space.

3. A method of measuring biochemical information using color space conversion, the method comprising:
acquiring an image of a urine test kit equipped with a biochemical sample rod including a pad cell, the urine test kit including a plurality of colorimetric table cells;
extracting a potential color of a first color space of the plurality of colorimetric table cells and the pad cell from the image;
extracting the potential color as a color of a color space other than the first color space;
selecting a colorimetric table cell having a color closest to any one of a plurality of pad cells of the other color space from among a plurality of colorimetric table cells;
diagnosing urine by determining a result index on the basis of a colorimetric table cell index having a color closest in the color space other than the first color space;
extracting the potential color of the first color space as a color of a randomly selected one of the second to $\ell$ th color spaces in the case of a randomly selected number, where $\ell$ is an integer of three or more;
finding $t^{th}$ color distances between a colorimetric table cell having a color closest in the $t^{th}$ color spaces, where $2 \leq t \leq \ell$, and colors obtained by converting the color of the pad cell into the colors of the $t^{th}$ color spaces and selecting a color space having the smallest color distance among the $t^{th}$ color distances;
determining a colorimetric table cell index having a color closest in the selected color space as the result index when the urine is diagnosed by determining the result index on the basis of the colorimetric table cell index having the color closest in the other cell space; and
deriving a final index by repeating the selecting of the color space and the determining of the result index a predetermined number N of times after re-determining any number $\ell$ and re-extracting a color of a colorimetric table cell and a pad cell extracted from the selected color space as the color of the randomly selected one of the second to $\ell$ th color spaces.

4. The method of claim 3, further comprising diagnosing the urine according to a final index that is most frequently derived by repeating the extracting of the potential color of the first color space as the color of the randomly selected one of the second to $\ell^{th}$ color spaces, the selecting of the color space, the determining of the result index, and the deriving of the final index.

5. The method of claim 1, wherein the extracting of the potential color comprises calculating a plurality of feature values through convolution of the color matrix and the convolution filter and extracting a value having the highest density from a histogram generated by the plurality of feature values as the potential color.

6. The method of claim 1, further comprising performing white-balancing such that the image having an inconstant color distribution has a constant color value.

7. The method of claim 6, wherein the performing of white-balancing comprises correcting a color variation of the image such that the image has certain color development regardless of external factors using a color constancy algorithm.

8. The method of claim 6, wherein the performing of white-balancing further comprises converting an image having an inconstant color value into a histogram; re-converting the histogram to be divided into predetermined displacement values; extracting rank values from the re-converted histogram; and implementing an image having a constant color value on the basis of the predetermined displacement values and the rank values, wherein the image having the constant color value is implemented using the following equation:

$$\frac{(Output_{max} - Output_{min}) \times (Input - Histogram_{min})}{Histogram_{max} - Histogram_{min}} + Output_{min}$$

where $Output_{max}$ indicates an extracted maximal displacement value, $Output_{min}$ indicates an extracted minimal displacement value, Input indicates an input value, $Histogram_{min}$ indicates a minimal histogram rank, and $Histogram_{max}$ indicates a maximal histogram rank.

9. The method of claim 1, wherein the first color space and the other color space includes at least one of RGB, HSV, $\ell_1\ell_2\ell_3$, $m_1m_2m_3$, and Lab.

10. The method of claim 1, further comprising combining the color matrix and a colorimetric table matrix generated using the potential color of the colorimetric table cell.

11. A non-transitory computer-readable recording medium having a program recorded thereon for performing the method of claim 1.

* * * * *